(12) United States Patent
Alghazi

(10) Patent No.: US 10,136,841 B2
(45) Date of Patent: Nov. 27, 2018

(54) MULTI-FUNCTIONAL SMART MOBILITY AID DEVICES AND METHODS OF USE

(71) Applicant: CAN Mobilities, Inc., San Jose, CA (US)

(72) Inventor: Ahmad AlSayed M. Alghazi, Campbell, CA (US)

(73) Assignee: CAN Mobilities, Inc., San Jose, CA (US)

( * ) Notice: Subject to any disclaimer, the term of this patent is extended or adjusted under 35 U.S.C. 154(b) by 0 days.

(21) Appl. No.: 15/128,440

(22) PCT Filed: Jun. 24, 2015

(86) PCT No.: PCT/US2015/022341
§ 371 (c)(1),
(2) Date: Sep. 23, 2016

(87) PCT Pub. No.: WO2015/148578
PCT Pub. Date: Oct. 1, 2015

(65) Prior Publication Data
US 2017/0172462 A1    Jun. 22, 2017

Related U.S. Application Data

(60) Provisional application No. 61/969,385, filed on Mar. 24, 2014.

(51) Int. Cl.
*A61B 5/00* (2006.01)
*A61B 5/11* (2006.01)
(Continued)

(52) U.S. Cl.
CPC ............... *A61B 5/11* (2013.01); *A45B 5/00* (2013.01); *A61B 5/0022* (2013.01);
(Continued)

(58) Field of Classification Search
CPC ......... A61B 5/11; A61B 5/112; A61B 5/6887; A61G 2203/30; A61G 2203/36; A61G 2203/42; A61H 3/02; G08B 21/0461
(Continued)

(56) References Cited

U.S. PATENT DOCUMENTS 5,490,825 A    2/1996  Wilkinson
5,973,618 A   10/1999  Ellis
(Continued)

FOREIGN PATENT DOCUMENTS

CN    202859592 U    4/2013
CZ     20100862 A3   6/2012
(Continued)

OTHER PUBLICATIONS

Braga et al.; Intelwheels:modular development platform for intelligent wheelchairs; Journal of Rehabilitation Research and Development; 48(9); pp. 1061-1077; Sep. 1, 2011.
(Continued)

*Primary Examiner* — Michael Carey
(74) *Attorney, Agent, or Firm* — Shay Glenn LLP

(57) ABSTRACT

Embodiments of a smart mobility aid device may have sensors to collect, monitor, analyze and represent data including but not limited to activity tracking, biometrics and safety and emergency features. The activity tracking include number of steps, miles, and activity speed, user pressure on a device, activity types and analysis. The user biometric data includes but is not limited to blood work, blood pressure, blood sugar, heart rate, oxygen level/rate, ECG, EMG, muscle strain, humidity, UV, body temperature. Additional features include an emergency button, fall detection, warnings, and user pattern analysis changes. The mobility aid device is connected to other smart electronic device and/or the Internet using but not limited to Bluetooth, Wi-Fi, and
(Continued)

Handle sensors or/and SIM card. The device gives the user or/and caregiver live feedback about user health metrics and status using a data representation method.

15 Claims, 13 Drawing Sheets

(51) Int. Cl.

| | |
|---|---|
| *A61G 5/10* | (2006.01) |
| *B62K 5/00* | (2013.01) |
| *B62K 5/025* | (2013.01) |
| *A61H 3/02* | (2006.01) |
| *G06Q 50/22* | (2018.01) |
| *G08B 21/04* | (2006.01) |
| *A45B 5/00* | (2006.01) |
| *A61B 5/0205* | (2006.01) |
| *G06F 19/00* | (2018.01) |
| *G16H 40/67* | (2018.01) |
| *A61J 7/04* | (2006.01) |
| *A61H 3/00* | (2006.01) |
| *A61H 3/04* | (2006.01) |

(52) U.S. Cl.
CPC ............ *A61B 5/0205* (2013.01); *A61B 5/112* (2013.01); *A61B 5/1118* (2013.01); *A61B 5/1123* (2013.01); *A61B 5/6887* (2013.01); *A61B 5/742* (2013.01); *A61G 5/10* (2013.01); *A61H 3/02* (2013.01); *B62K 5/00* (2013.01); *B62K 5/025* (2013.01); *G06F 19/00* (2013.01); *G06Q 50/22* (2013.01); *G08B 21/0461* (2013.01); *G16H 40/67* (2018.01); *A45B 2200/05* (2013.01); *A61B 2503/08* (2013.01); *A61B 2560/0431* (2013.01); *A61G 2203/16* (2013.01); *A61G 2203/20* (2013.01); *A61G 2203/30* (2013.01); *A61G 2203/34* (2013.01); *A61G 2203/36* (2013.01); *A61G 2203/42* (2013.01); *A61H 3/04* (2013.01); *A61H 2003/006* (2013.01); *A61H 2201/0188* (2013.01); *A61H 2201/5012* (2013.01); *A61H 2201/5015* (2013.01); *A61H 2201/5043* (2013.01); *A61H 2201/5046* (2013.01); *A61H 2201/5048* (2013.01); *A61H 2201/5064* (2013.01); *A61H 2201/5097* (2013.01); *A61H 2230/04* (2013.01); *A61H 2230/06* (2013.01); *A61H 2230/202* (2013.01); *A61H 2230/207* (2013.01); *A61H 2230/30* (2013.01); *A61H 2230/40* (2013.01); *A61H 2230/42* (2013.01); *A61H 2230/50* (2013.01); *A61H 2230/60* (2013.01); *A61H 2230/65* (2013.01); *A61J 7/0481* (2013.01)

(58) Field of Classification Search
USPC .................................................. 600/300, 301
See application file for complete search history.

(56) References Cited

U.S. PATENT DOCUMENTS

| | | | |
|---|---|---|---|
| 6,668,846 | B2 | 12/2003 | Meador |
| 6,745,786 | B1 | 6/2004 | Davis |
| 6,774,795 | B2 | 8/2004 | Eshelman et al. |
| 7,965,196 | B2 | 6/2011 | Liebermann |
| 8,015,972 | B2 | 9/2011 | Pirzada |
| 8,418,705 | B2 | 4/2013 | Ota et al. |
| 8,740,240 | B1 | 6/2014 | Merel |
| 8,812,231 | B1 | 8/2014 | Brickous |
| 8,862,307 | B2 | 10/2014 | Pettersson et al. |
| 8,881,852 | B2 | 11/2014 | Kim |
| 8,974,232 | B2 | 3/2015 | Behrenbruch et al. |
| 2001/0007450 | A1* | 7/2001 | Begum ................. B62B 3/1408 345/204 |
| 2005/0014607 | A1 | 1/2005 | Olkkonen |
| 2006/0108426 | A1 | 5/2006 | Hopkins |
| 2007/0085690 | A1* | 4/2007 | Tran ....................... A61B 5/103 340/573.1 |
| 2008/0072940 | A1 | 3/2008 | Cheng et al. |
| 2008/0251110 | A1 | 10/2008 | Pede |
| 2011/0205081 | A1 | 8/2011 | Chen et al. |
| 2012/0310470 | A1 | 12/2012 | Holenweg et al. |
| 2012/0318311 | A1* | 12/2012 | Alghazi ................... A61H 3/04 135/66 |
| 2013/0041507 | A1* | 2/2013 | Ota .......................... A61H 3/04 700/258 |
| 2013/0093852 | A1 | 4/2013 | Ye |
| 2013/0218053 | A1 | 8/2013 | Kaiser et al. |

FOREIGN PATENT DOCUMENTS

| | | |
|---|---|---|
| DE | 202011002974 U1 | 10/2011 |
| EP | 1943919 A2 | 7/2008 |
| KR | 20110133879 A | 12/2011 |

OTHER PUBLICATIONS

Lan et al.; Smartfall: an automatic fall detection system based on subsequence matching for the smartcane; InProceedings of the Fourth International Conference on Body Area Networks; ICST (Institute for Computer Sciences, Social-Informatics and Telecommunications Engineering; 8 pages; Apr. 1, 2009.

Mercado et al.; Smart cane: instrumentation of a quad cane with audio-feedback monitoring system for partial weightbearing support; IEEE International Symposium on Bioelectronics and Bioinformatics (ISBB); pp. 1-4; Apr. 11, 2014.

Mlot; Fujitsu smart cane helps seniors stay mobile safe; PC Magazine Online; 2 pages; Mar. 1, 2013 (Full Text Version).

Pole; Sherbrooke native develops smart walker to prevent falls; Infomart, a division of Postmedia Network Inc.; Sherbrooke, Que, Canada; 3 pages; Jul. 12, 2010 (Full Text Version).

\* cited by examiner

Handle sensors

Sensors module diagram

Automatic lifting mechanism

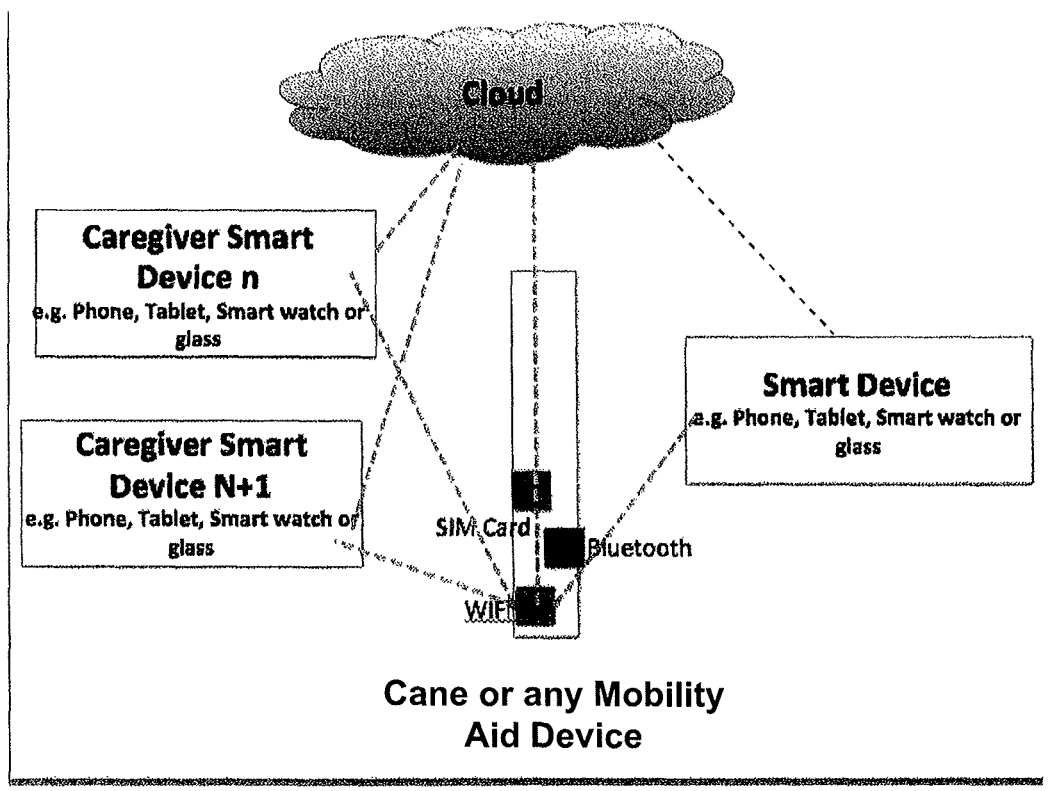
Figure 4: Wi-Fi communication

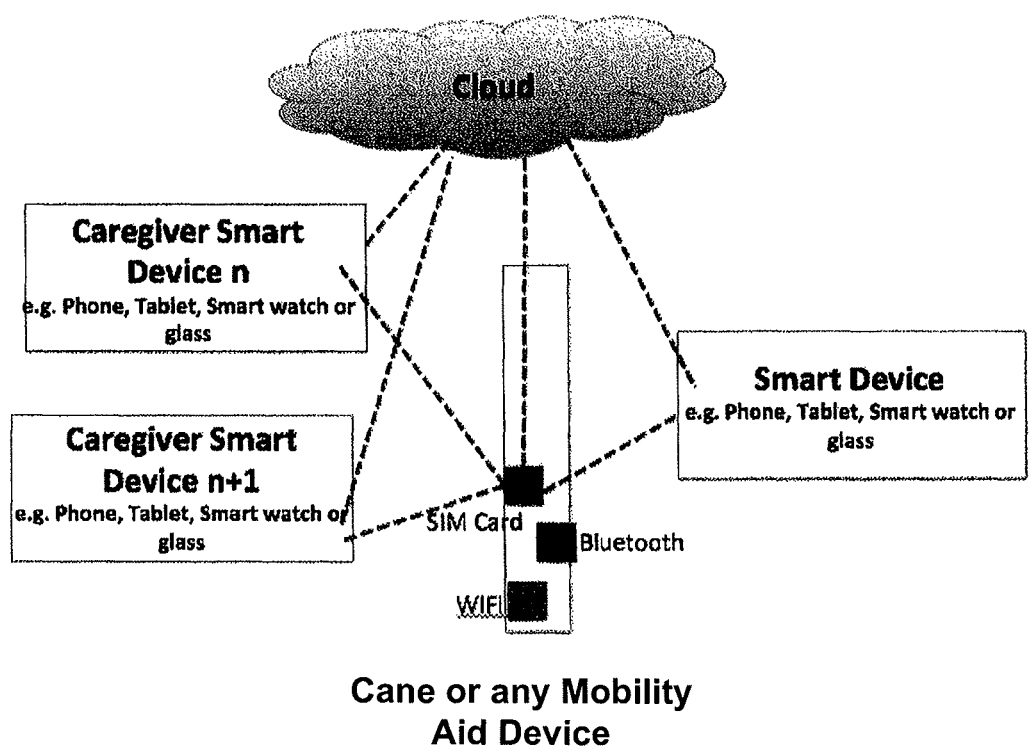
Figure 5: SIM card communication

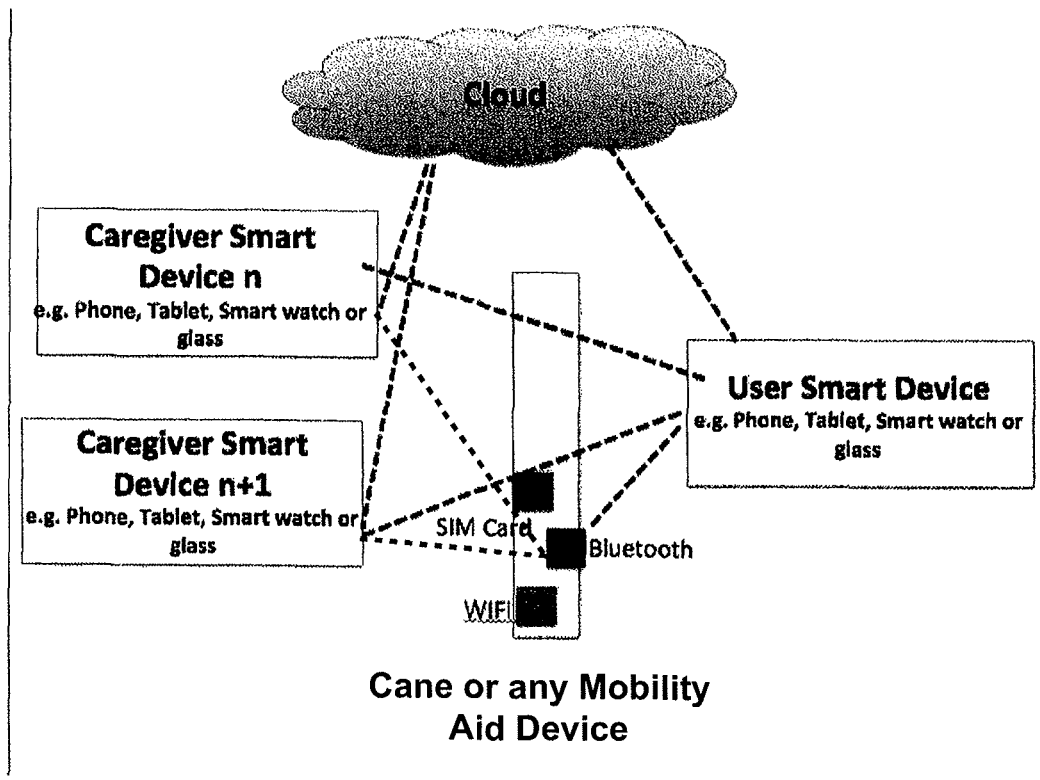
Figure 6: Bluetooth communication

Cross Section for the pin and the shaft

MULTI-FUNCTIONAL SMART MOBILITY AID DEVICES AND METHODS OF USE

CROSS REFERENCE TO RELATED APPLICATIONS

This application claims the benefit of U.S. Provisional Patent Application No. 61/969,385, filed Mar. 24, 2014, titled "MULTIFUNCTIONAL SMART CANE," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application relates to enhanced capability mobility aid devices including canes, walkers, crutches, scooters and wheelchairs.

BACKGROUND

A variety of different types of mobility aid devices have been described. While some of these devices have capabilities useful to the person receiving aid, still more capabilities are needed.

SUMMARY OF THE DISCLOSURE

In general, in one embodiment, a smart mobility device includes a handle adapted to be gripped by a user of the smart mobility device; a display built into the handle wherein the display is visible to the user while the user is gripping the handle; one or more activity tracking components carried by the smart mobility device for collecting information about the user's daily activity; an electronic memory for storing the collected information about the user's daily activity; and one or more electronic communication components to transmit the user's daily activity from the electronic memory in the smart mobility device to another electronic device.

This and other embodiments can include one or more of the following features. In one aspect, the display can include a touch screen. In another aspect, the smart mobility device can further include a GPS component and including turn-by-turn visual guidance on the display, by voice output on a speaker on the smart mobility device or by vibration output to the smart mobility device user. In a further aspect, the handle can include a gripping sensor used to power on and power off the smart mobility device when the smart mobility device user grips the gripping sensor. In an alternative aspect, the one or more electronic components can be a SIM card, a Wi-Fi communications module or a Bluetooth communications module. In yet another aspect, the one or electronic communication components can provide communication using a cellular network, an app push notification, a third party update or a website update. In still another aspect, in use the smart mobility device user can receive applications and services from a cloud based software platform via the smart mobility device. In one aspect, in use the smart mobility device user can order and receive services from a cloud based software platform via the smart mobility device. In another aspect, in use the smart mobility device user can order and receive services from a cellular network via the smart mobility device. In a further aspect, in use the smart mobility device user can receive applications and services from an application store via the smart mobility device. In an alternative aspect, the one or electronic communication components can provide for entering user data into the smart mobility device using a smart device. In yet another aspect, the smart device can be a smartphone, a smart watch, a smart glass, a tablet, a laptop or a computer. In still another aspect, in use the display can provide information about the user progress on a game based on user targets. In one aspect, in use the display can provide information about the result of a social game wherein the user's activity tracking can be compared to another user. In another aspect, the memory can contain information about a daily activity pattern of the smart mobility device user. In a further aspect, the daily activity pattern can be a notification for the smart mobility device user's medication schedule. In an alternative aspect, the notification can be sent automatically from the smart mobility device to a caregiver, a doctor or an involved party. In yet another aspect, the smart mobility device can be adapted and configured for use with a mobile payment system. In still another aspect, a rechargeable battery within the smart mobility device can be adapted and configured for wireless charging. In another aspect, a rechargeable battery within the smart mobility device can be adapted and configured for charging via a self-plugging magnetic plug. In one aspect, a rechargeable battery within the smart mobility device can be adapted and configured for wireless charging when a portion of the smart mobility aid device is placed on a charging pad configured to charge the smart mobility device. In another aspect, the smart mobility device can further include a sensor for detecting a biometric measurement of the smart mobility device user selected from blood work, blood pressure, blood sugar, heart rate, oxygen level/rate, ECG, EMG, muscle strain, humidity, UV or body temperature. In a further aspect, the smart mobility device can further include one or more smart mobility device user activity tracking components selected from an accelerometer, a gyroscope, a MEMS magnetometer, a barometric pressure sensor, a temperature sensor, a microcontroller, a flash memory, a digital motion processor, a motion processing library or a Bluetooth low energy radio component. In an alternative aspect, the smart mobility device can further include the functions of a linear acceleration, a heading, an altitude, a temperature, an angular velocity, or an angular position. In yet another aspect, the smart mobility device can be adapted and configured as a cane. In still another aspect, the smart mobility device can be adapted and configured as a walker. In a further aspect, the smart mobility device can be adapted and configured as a crutch. In one aspect, the smart mobility device can be adapted and configured as a scooter. In another aspect, the smart mobility device can be adapted and configured as a wheelchair. In a further aspect, the smart mobility device can further include a fingerprint sensor. In an alternative aspect, the smart mobility device can be used by the smart mobility device user as a payment method for services available from a software platform or an app store. In yet another aspect, the smart mobility device can be integrated with a mobile payment system. In still another aspect, the smart mobility device can further include an emergency button that when pressed establishes communications with one or more of a caregiver or an 911 emergency service.

In general, in one embodiment, a multifunctional smart cane includes a handle adapted to be gripped by a hand of a user; a body having a base on one end and coupled to the handle on the other; a screen built into the handle wherein the screen is visible to the user while gripping the handle; one or more activity tracking components carried by the smart cane for collecting information about the user's daily activity; an electronic memory for storing the collected information about the user's daily activity; and one or more electronic communication components to transmit the user's daily activity from the electronic memory in the smart cane to another electronic device.

This and other embodiments can include one or more of the following features. In one aspect, the display can be a touch screen. In another aspect, the smart cane can further include a GPS component and including turn-by-turn visual guidance on the display, by voice output on a speaker on the smart cane or by vibration output to the smart cane user. In a further aspect, the handle can include a gripping sensor used to power on and power off the smart cane when the smart cane user grips the gripping sensor. In an alternative aspect, the one or more electronic components can be a SIM card, a Wi-Fi communications module or a Bluetooth communications module. In yet another aspect, the one or electronic communication components can provide communication using a cellular network, an app push notification, a third party update or a website update. In still another aspect, in use the smart cane user can receive applications and services from a cloud based software platform via the smart cane. In one aspect, in use the smart cane user can receive applications and services from an application store via the smart cane. In another aspect, the one or electronic communication components can provide for entering user data into the smart cane using a smart device. In a further aspect, the smart device can be a smartphone, a smart watch, a smart glass or a tablet. In an alternative aspect, in use the display can provide provides information about the user progress on a game based on user targets. In yet another aspect, in use the display can provide information about the result of a social game wherein the user's activity tracking is compared to another user. In still another aspect, the memory can contain information about a daily activity pattern of the smart cane user. In one aspect, the daily activity pattern can be a notification for the smart cane user's medication schedule. In another aspect, the notification can be sent automatically from the smart cane to a caregiver, a doctor or an involved party. In a further aspect, the smart cane can be adapted and configured for use with a mobile payment system. In an alternative aspect, a rechargeable battery within the smart cane can be adapted and configured for wireless charging. In yet another aspect, a rechargeable battery within the smart cane can be adapted and configured for charging via a self-plugging magnetic plug. In still another aspect, a rechargeable battery within the smart cane can be adapted and configured for wireless charging when a portion of the smart mobility aid device is placed on a charging pad configured to charge the smart cane. In one aspect, the smart cane can further include a sensor for detecting a biometric measurement of the smart cane user selected from blood work, blood pressure, blood sugar, heart rate, oxygen level/rate, ECG, EMG, muscle strain, humidity, UV or body temperature. In another aspect, the smart cane can further include one or more smart cane user activity tracking components selected from an accelerometer, a gyroscope, a MEMS magnetometer, a barometric pressure sensor, a temperature sensor, a microcontroller, a flash memory, a digital motion processor, a motion processing library or a Bluetooth low energy radio component. In a further aspect, the smart cane can further include the functions of a linear acceleration, a heading, an altitude, a temperature, an angular velocity, or an angular position.

In general, in one embodiment, a multifunctional smart cane includes a handle adapted to be gripped by a hand of the smart cane user; a body having a base on one end and coupled to the handle on the other; a fingerprint sensor on the handle configured for identification of a fingerprint of the smart cane user, one or more activity tracking components carried by the smart cane for collecting information about the user's daily activity; and an electronic memory for storing the collected information about the user's daily activity.

This and other embodiments can include one or more of the following features. In one aspect, the smart cane can further include a display on the handle wherein the display is visible to the user while gripping the handle. In another aspect, the smart cane can further include one or more electronic communication components to transmit the user's daily activity from the electronic memory in the smart cane to another electronic device. In a further aspect, the fingerprint sensor can be adapted and configured to permit smart cane user account access. In an alternative aspect, the fingerprint sensor can be adapted and configured to permit smart cane user activity tracking. In yet another aspect, the display can be a touch screen. In still another aspect, the smart cane can further include a GPS component and can include turn-by-turn visual guidance on the display, by voice output on a speaker on the smart cane or by vibration output to the smart cane user. In one aspect, the handle can include a gripping sensor used to power on and power off the smart cane when the smart cane user grips the gripping sensor. In another aspect, the one or more electronic components can be a SIM card, a Wi-Fi communications module or a Bluetooth communications module. In a further aspect, the one or more electronic communication components can provide communication using a cellular network, an app push notification, a third party update or a website update. In an alternative aspect, in use the smart cane user can receive applications and services from a cloud based software platform via the smart cane. In yet another aspect, in use the smart cane user can receive applications and services from an application store via the smart cane. In still another aspect, the one or more electronic communication components can provide for entering user data into the smart cane using a smart device. In one aspect, the smart device can be a smartphone, a smart watch, a smart glass or a tablet. In another aspect, the memory can contain information about a daily activity pattern of the smart cane user. In a further aspect, the daily activity pattern can be a notification for the smart cane user's medication schedule. In an alternative aspect, the notification can be sent automatically from the smart cane to a caregiver, a doctor or an involved party. In yet another aspect, the smart cane can be adapted and configured for use with a mobile payment system. In still another aspect, the smart cane can further include a sensor for detecting a biometric measurement of the smart cane user selected from blood work, blood pressure, blood sugar, heart rate, oxygen level/rate, ECG, EMG, muscle strain, humidity, UV or body temperature. In one aspect, the one or more smart cane user activity tracking components can be selected from an accelerometer, a gyroscope, a MEMS magnetometer, a barometric pressure sensor, a temperature sensor, a microcontroller, a flash memory, a digital motion processor, a motion processing library or a Bluetooth low energy radio component. In another aspect, the smart cane can further include the functions of a linear acceleration, a heading, an altitude, a temperature, an angular velocity, or an angular position. In a further aspect, the cane can include a light operable by a light sensor. In an alternative aspect, the light can come on automatically when the light sensor detects darkness. In yet another aspect, the cane can include a glowing color selected to aid in finding the cane in the dark. In still another aspect, the cane can be adapted and configured to be folded to reduce its size. In one aspect, the smart cane can further include an unfolding button that can cause the cane to automatically fold or unfold. In another aspect, the cane can be adapted and configured to generate a sound to aid in being located by the smart cane user. In a further aspect, the cane can be adapted and configured for being located using a GPS system working with a smart device. In an alternative aspect, the smart cane can further include a base changing mechanism allowing for removal of one base type and replacement with another base type. In yet another aspect, a user preference can determine the removal of one base type and the replacement of another base type. In still another aspect, a smart cane advice can determine the removal of one base type and the replacement of another base type. In one aspect, the one base type and the another base type can be selected from a basic base, a tripod base, a flexible base and an ice tip base. In another aspect, the smart cane can further include an emergency button that when pressed establishes communications with one or more of a caregiver or an 911 emergency service.

In general, in one embodiment, a method of using a smart mobility assistance device for tracking the activity of a person using the smart mobility assistance device includes collecting data from one or more health monitoring sensors placed on the smart mobility assistance device for monitoring a health parameter of the person during a regular use of the smart mobility assistance device; analyzing the data from the collecting step; and representing a recommendation for the person or any involved party based on the analyzing step.

This and other embodiments can include one or more of the following features. In one aspect, the one or more health monitoring sensors can include a sensor for detecting one or more biometrics of the person using the smart mobility assistance device. In another aspect, the health parameter of the person can be one or more of a blood pressure, a heart rate, an oxygen level, an oxygen rate, an ECG, an EMG, a muscle strain, or a body temperature. In a further aspect, the regular use can be walking, stepping, tapping, or using the smart mobility aid device for creating a daily pattern of activity. In an alternative aspect, the regular use can include an activity tracking of the smart mobility device user. In yet another aspect, the activity tracking can include counting the number of steps taken by the smart mobility aid user. In still another aspect, the activity tracking can include recording an activity speed. In one aspect, the mobility assistance device can be a smart cane and the activity tracking can include monitoring a motion sensor and a pressure sensor on the cane. In another aspect, the collecting step can further include determining a current activity is initiated using a motion sensor. In a further aspect, the method can provide a time when the current activity is initiated and recording the duration of the current activity. In an alternative aspect, the current activity can be walking, running, sitting, watching TV or going to the bathroom. In yet another aspect, the collecting step can further include entering information about the person using the smart assistive mobility aid device using a screen on the mobility aid device. In still another aspect, the collecting step can further include entering information about the person using the smart assistive mobility aid device using one or more smart devices. In one aspect, the one or more smart devices can be a smart phone, a smart watch, a pair of smart glasses or a tablet. In another aspect, the step of representing collected information and data can be performed on a smart phone. In a further aspect, representing can include recommendation to use a different smart mobility aid device. In an alternative aspect, the recommendation can include transitioning a person using a smart mobility cane to using a smart mobility walker. In yet another aspect, the analyzing the data step can be performed on the smart mobility aid device, on a smart device in communication with mobility device or on a remote server. In still another aspect, the analyzing step can include performing a predictive analysis. In one aspect, the analyzing step can include using an artificial intelligence algorithm. In another aspect, the representing step can include providing the user or any involved party with live feedback on the user's performance using the smart mobility aid device. In a further aspect, the representing step can include providing the user with live motivational feedback based on performance towards activity targets. In an alternative aspect, the representing step can include providing the user feedback based on comparison to other smart mobility aid device users via social gaming. In yet another aspect, the method can further include using an artificial intelligence algorithm with input from motion sensors to differentiate between a falling smart mobility aid user and a dropping smart mobility aid device. In still another aspect, in the case of a falling smart mobility aid user there can be a step of providing an emergency notification to caregiver or providing an alarm or calling an 911 emergency service provider. In one aspect, the method can further include creating a daily activity pattern of the smart mobility aid device user from collected information about the smart mobility aid device user's activities with the smart mobility aid device. In another aspect, the method can further include detecting an input from a distance sensor, the representing step including warning the user of the object or obstacle detected by the distance sensor. In a further aspect, the representing can further include providing turn by turn visual, voice or vibration guidance based on a GPS sensor provided by the smart mobility aid device. In an alternative aspect, the representing can further include providing a health status indicator of the person using the smart mobility aid device. In yet another aspect, the indicator can be provided in the form of a light, an LED light, a sound, a vibration, or a glyph. In still another aspect, a portion of the collecting step, the analyzing step or the representing step can further include communicating a portion of the collected data to another device using a communications module on the smart mobility aid device. In one aspect, the another device can be a smart phone, a smart watch, a tablet or a smart glasses. In another aspect, the method can further include communicating the collected information and data of the smart mobility aid device to the person using the smart mobility aid device using a built in screen on the mobility aid device, a touch screen, a voice command from a speaker on the smart mobility aid device, by a vibration generated by the mobility aid device, or using a different electronic device. In a further aspect, the different electronic device can include a smart phone, a smart watch or a smart glasses. In an alternative aspect, the method can further include using a fingerprint sensor for identifying the person using the smart mobility aid device. In yet another aspect, the method can further include using a fingerprint sensor for signing in or signing out of an account assigned to the person using the smart mobility aid device. In still another aspect, the method can further include using a fingerprint sensor for tracking the activities of the person using the smart mobility aid device. In one aspect, the method can further include integrating the smart mobility aid device with a mobile payment system and using the smart mobility aid device as a payment method for services.

In general, in one embodiment, a smart mobility aid device having activity tracking and monitoring capabilities includes a first sensor configured to detect motion of the device corresponding to rotation, shake, linear acceleration, heading, angular velocity, or angular position while the mobility aid device is in contact with a person using the device; a second sensor configured to detect at least one biometric parameter of the person using the device; and a processor in communication with the first and second sensors that utilizes an algorithm to discriminate between the smart device user falling and the smart device falling based on data received from the first and second sensors.

This and other embodiments can include one or more of the following features. In one aspect, the device can further include a server in communication with the device and located remotely from the device. In another aspect, the first sensor can be selected from the group consisting of an accelerometer, gyroscope, and MEMS magnetometer. In a further aspect, the smart mobility aid device can be a smart cane and the first sensor is positioned within the cane. In an alternative aspect, the second sensor can be positioned within a handle of the cane such that in use the second sensor is in contact with the patient. In yet another aspect, the at least one biometric parameter can be selected from the group consisting of blood pressure and heart rate. In still another aspect, the second sensor can be configured to detect a weight imparted by the patient upon the device. In one aspect, the motion detected by the first sensor can be selected from the group consisting of walking, running, standing up, sitting down, and falling. In another aspect, the smart mobility aid device can be configured as a cane, a walker, a wheelchair, a scooter, or a crutch. In a further aspect, the device can be configured to be in wireless communication with a remote party. In an alternative aspect, the processor can be programmed to initiate contact with the remote party when triggered by a predetermined parameter. In yet another aspect, the device can further include a third sensor in communication with the processor and which can be configured to detect an audio signal from the patient. In still another aspect, the device can further include a third sensor in communication with the processor and which can be configured to detect an ambient light level and a light in communication with the third sensor. In one aspect, the device can further include a user interface in communication with the processor.

In general, in one embodiment, a method of monitoring a person using a smart mobility aid device includes detecting a motion of the person via a first sensor incorporated into the smart mobility device in use by the person, wherein the motion corresponds to one or more of rotation, shake, linear acceleration, heading, angular velocity, or angular position while the mobility aid device is in contact with a person using the device; receiving an input via a second sensor incorporated into the smart mobility aid device; determining if the person using the smart mobility aid device has fallen via a processor in communication with the first and second sensors based on data received from the first and second sensors; and transmitting information relating to the fallen person to a server located remotely from the person using the smart mobility aid device.

This and other embodiments can include one or more of the following features. In one aspect, the step of detecting a motion can be performed using a first sensor selected from the group consisting of an accelerometer, gyroscope, and MEMS magnetometer. In another aspect, receiving the input via a second sensor can include detecting at least one biometric parameter of the person. In a further aspect, detecting at least one biometric parameter can include detecting blood pressure or heart rate. In an alternative aspect, transmitting information can include transmitting to a server in communication with the processor and located remotely from the housing. In yet another aspect, the first sensor can be positioned within or carried by a smart mobility aid device configured as a cane configured to be held by the person. In still another aspect, the second sensor can be positioned within a handle of the cane such that in use the second sensor can be in contact with the person using the smart mobility aid device. In one aspect, detecting at least one biometric parameter can include detecting a weight imparted by the patient upon the smart mobility aid device. In another aspect, detecting a motion can include detecting the motion selected from the group consisting of walking, running, standing up, sitting down, and falling. In a further aspect, the smart mobility aid device can be selected from the group consisting of a cane, a walker, a wheelchair, a scooter, or a crutch. In an alternative aspect, transmitting can include transmitting the information when triggered by a predetermined parameter. In yet another aspect, the method can further include detecting an audio signal from the patient via a third sensor in communication with the processor. In still another aspect, the method can further include detecting an ambient light level via a third sensor in communication with the processor. In one aspect, the method can further include displaying the information via a user interface in communication with the processor.

In general, in one embodiment, a method of monitoring a person using a smart mobility aid device includes receiving an input via a first sensor incorporated into the smart mobility aid device; determining if the person using the smart mobility aid device has fallen via a processor in communication with the first sensor based on data received from the first sensor; and transmitting information relating to the fallen person to a server located remotely from the person using the smart mobility aid device.

This and other embodiments can include one or more of the following features. In one aspect, the method can further include detecting a motion of the person via a second sensor incorporated into the smart mobility device in use by the person, wherein the motion corresponds to one or more of rotation, shake, linear acceleration, heading, angular velocity, or angular position while the mobility aid device is in contact with a person using the device. In another aspect, the determining step can include input from the second sensor. In a further aspect, the step of detecting a motion can be performed using a second sensor selected from the group consisting of an accelerometer, gyroscope, and MEMS magnetometer. In an alternative aspect, receiving the input via a first sensor can include detecting at least one biometric parameter of the person. In yet another aspect, detecting at least one biometric parameter can include detecting blood pressure or heart rate. In still another aspect, transmitting information can include transmitting to a server in communication with the processor and located remotely from the housing. In one aspect, the second sensor can be positioned within or carried by a smart mobility aid device configured as a cane configured to be held by the person. In another aspect, the first sensor can be positioned within a handle of the cane such that in use the second sensor can be in contact with the person using the smart mobility aid device. In a further aspect, detecting at least one biometric parameter can include detecting a weight imparted by the patient upon the smart mobility aid device. In an alternative aspect, detecting a motion can include detecting the motion selected from the group consisting of walking, running, standing up, sitting down, and falling. In yet another aspect, the smart mobility aid device can be selected from the group consisting of a cane, a walker, a wheelchair, a scooter, or a crutch. In still another aspect, transmitting can include transmitting the information when triggered by a predetermined parameter. In one aspect, the method can further include detecting an audio signal from the patient via a third sensor in communication with the processor. In another aspect, the method can further include detecting an ambient light level via a third sensor in communication with the processor. In a further aspect, the method can further include displaying the information via a user interface in communication with the processor.

In one aspect, a smart mobility aid device can be adapted and configured to alarm, notify, and/or remind a mobility aid device user or interested party about a smart mobility device user medication schedule using a voice reminder, a vibration reminder and/or an on screen reminder.

In another aspect, when a mobility aid device user takes a medication according to a medication schedule a caregiver or any involved parties can be notified.

In a further aspect, the medication schedule of a smart mobility aid device user can be modified, entered, managed, updated and/or tracked by the mobility aid device user, a caregiver or a doctor.

In yet another aspect, a smart mobility aid device can be adapted and configured to communicate and connect to a regular medicine container or a smart medication container.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4 is a diagram of Wi-Fi communications for a mobility device embodiment.

FIG. 5 is a diagram of SIM card communications for a mobility device embodiment.

FIG. 6 is a diagram of a Bluetooth communications for a mobility device embodiment.

DETAILED DESCRIPTION

Numerous alternative embodiments of a multi-functional smart and connected mobility aid device are described herein. Such device may help make users more independent and healthier. Smart mobility aid devices have sensors to collect, monitor, analyze and represent data including but not limited to activity tracking, biometrics and safety and emergency features. The activity tracking include number of steps, miles, and activity speed, user pressure on a smart cane or other device, activity types and analysis. The biometrics data including but not limited to blood work, blood pressure, blood sugar, heart rate, oxygen level/rate, ECG, EMG, muscle strain, humidity, UV, body temperature. The safety and emergency includes emergency button, falls detection and warnings, and user activity pattern collection and analysis of activity pattern changes. The sensors are placed on the handle/s to collect and monitor the data automatically, in some embodiments. Also, there are smart mobility aid embodiments that include a medication management system that reminds and monitors a user medication schedule. The smart mobility aid device data represented can be in form of visuals, sound/voice, or vibrations. The smart mobility aid device is connected to other devices and/or the Internet using ways including but not limited to Bluetooth, Wi-Fi, and or/and SIM card. In addition, a smart mobility aid device can analyze how a user walks using the device and advise a user to improve his walking pattern.

The device can be turned on/off automatically once a user grips the handle. The smart cane can be folded/unfolded manually or automatically. A smart mobility device may have a light that can be turned on automatically in dark places. The device may have a small light or a glowing color that helps user find the can in the dark. A smart mobility device may give the user or/and caregiver live feedback about user health metrics and status using data representation or other suitable communication method.

A smart mobility device can be charged by a self-charging mechanism, or by using a wire/wireless charger. The device also includes a base changing mechanism that allows a user to change the base according to a user preference, the condition of the user and the environment it will be used on or a device recommendation.

Figure 1A:
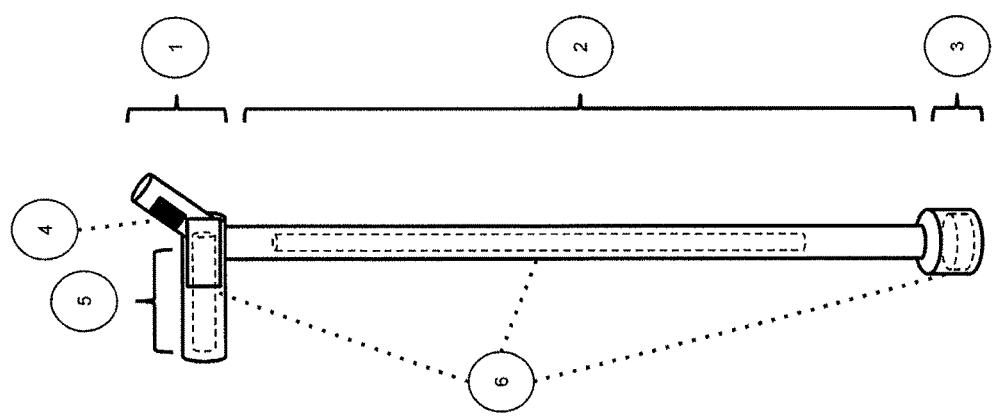
FIG. 1A is a view of a mobility assistance device alternative configured as a cane.
Figure 1B:
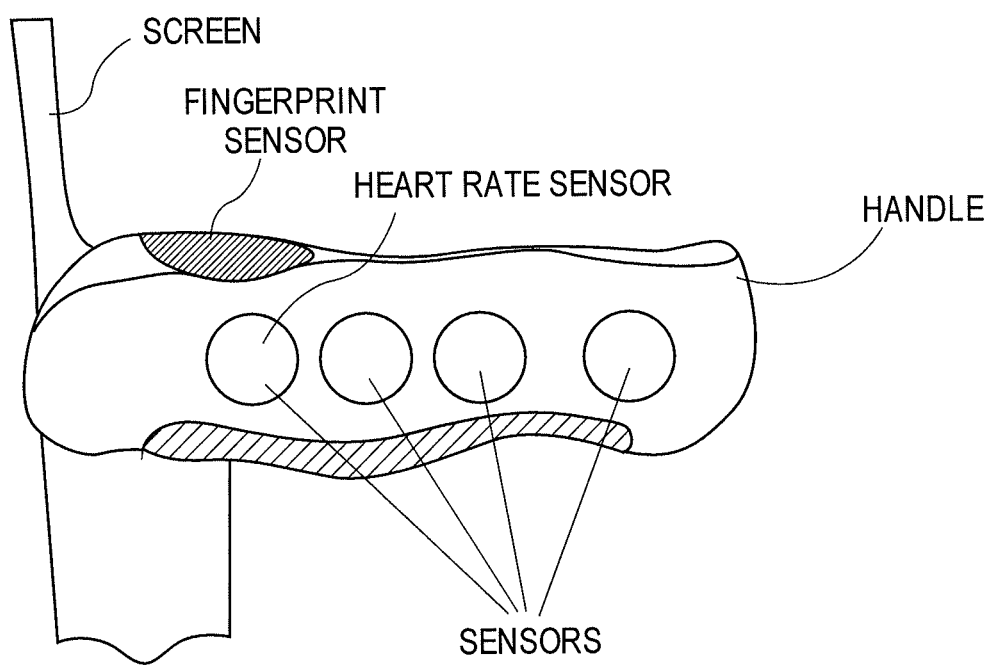
FIG. 1B is a close up view of an alternative handle embodiment of a mobility assistance device alternative configured as a cane (i.e., a smart cane).

FIGS. 1A and 1B show embodiments of a smart mobility aid device configured as a smart cane. The smart mobility aid device in FIG. 1A is a smart cane embodiment. FIG. 1A illustrates a cane that consists of a body (2) having a base (3) on one end and coupled to the handle (1) on the other end. The handle consists of a gripping area for the user's hand (5) and a screen (4) visible to the user while gripping the handle. The electronics, such as activity and biometrics tracking components, electronic memory, and communications components, can be built into the handle, body, or base of the device (6).

A multi functional cane that includes the following:

The Handle:

The handle can be in different shapes and used on different assistive mobility devices including but not limited to canes, walkers, crutches, scooters and wheelchairs.

Figure 1C:
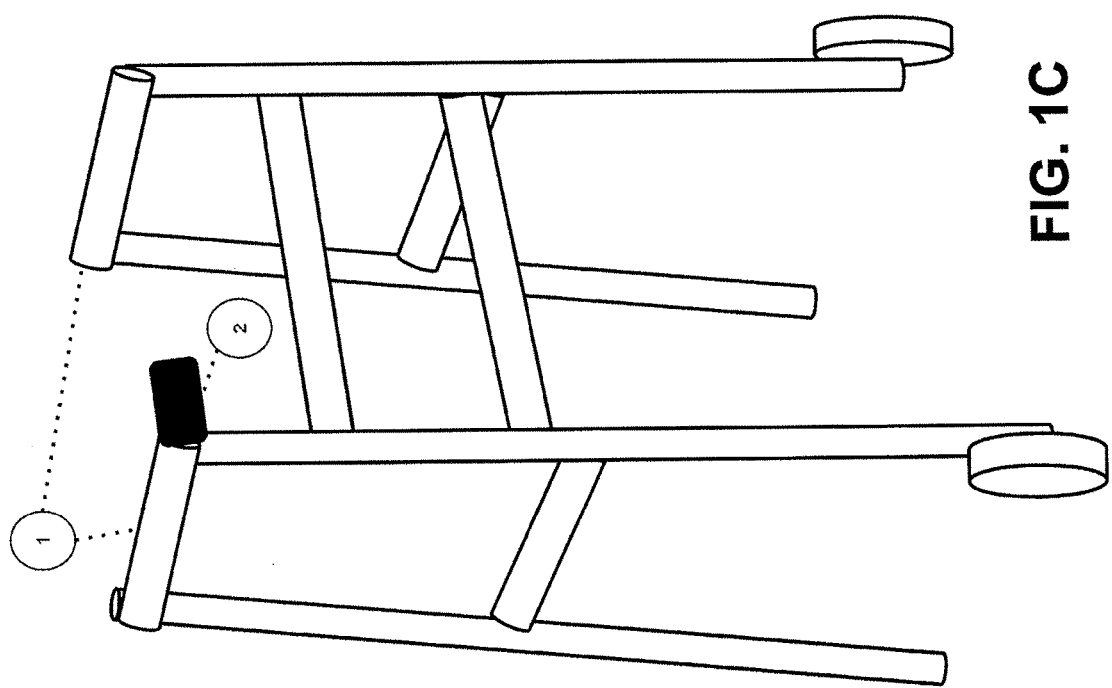
FIG. 1C is a perspective view of a mobility assistance device alternative configured as a walker (i.e., a smart walker).

The smart mobility aid device depicted in FIG. 1C is a walker embodiment. The handle (1) is grasped by the user and includes a display (2) visible to the user during use. The electronics, such as activity and biometrics tracking components, electronic memory, and communications components, can be built into the handle, body, or base of the device.

Figure 1D:
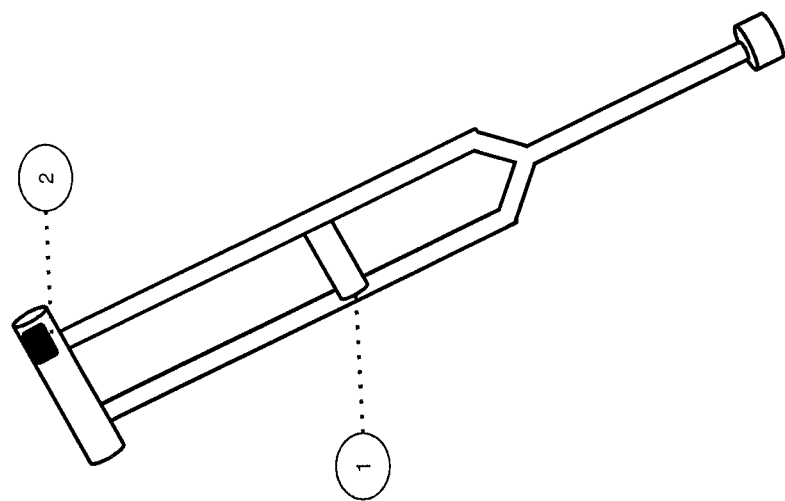
FIG. 1D is a perspective view of a mobility assistance device configured as a crutch (i.e., a smart crutch).

The smart mobility aid device depicted in FIG. 1D is a crutch embodiment. The handle (1) is grasped by the user. The display (2) is located beneath and in front of the user's shoulder during normal use. The electronics, such as activity and biometrics tracking components, electronic memory, and communications components, can be built into the handle, body, or base of the device.

Figure 1E:
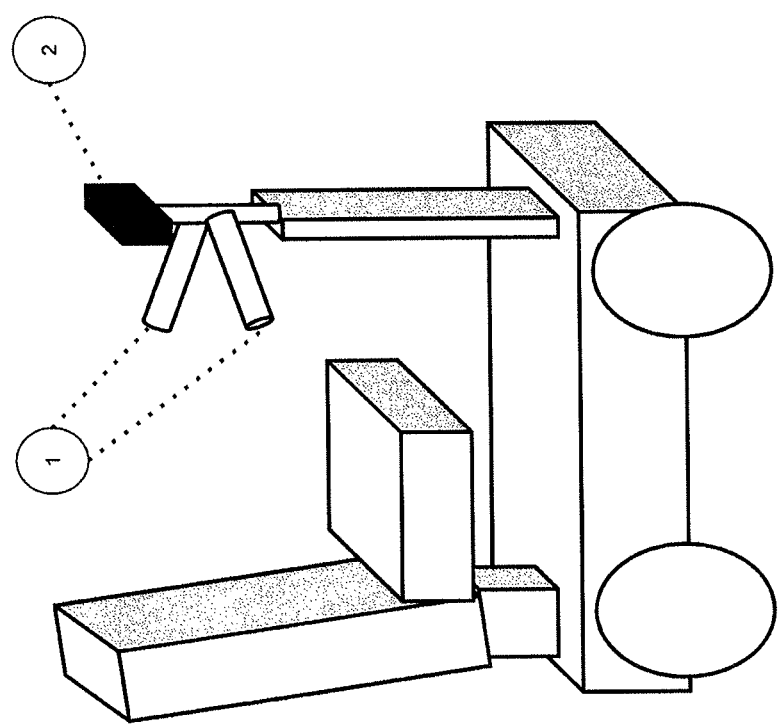
FIG. 1E is a perspective view of a mobility assistance device configured as a scooter (i.e., a smart scooter).

The smart mobility aid device depicted in FIG. 1E is a scooter embodiment. The handle (1) is grasped by the user and used to direct the scooter. The display (2) is located above the gripping area of the handles and in the line of sight of the user. The electronics, such as activity and biometrics tracking components, electronic memory, and communications components, can be built into the device, including the handle, body, or base.

Figure 1F:
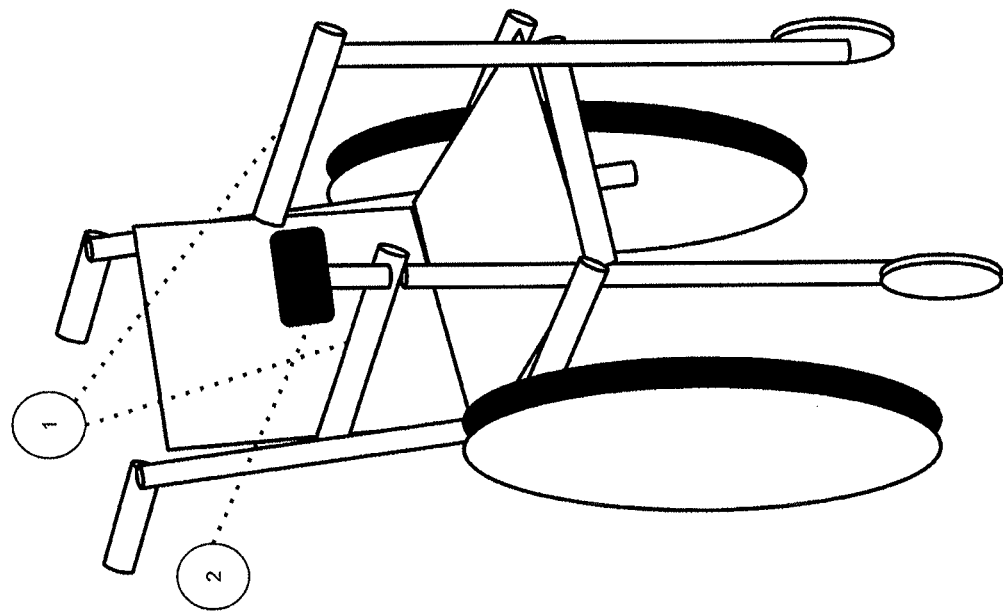
FIG. 1F is a perspective view of a mobility assistance device configured as a wheelchair (i.e., a smart wheelchair).

The smart mobility aid device FIG. 1F is a wheelchair embodiment. The handle (1) is used as an armrest or hand hold. The display (2) is located above the handle area of the handles and in the line of sight of the user. The electronics, such as activity and biometrics tracking components, electronic memory, and communications components, can be built into the device, including the handle, body, or base.

The handle can include different smart components including but not limited to: health monitoring sensors, sensors that detect biometrics of the person using the mobility device, a gripping sensor, a light sensor, a finger print sensor, a GPS component and a mobility device user health status indicator.

Health Monitoring Sensors:

In some embodiments, all the sensors are precisely placed in the handle of the cane so that it can monitor the user's health parameter during a regular use of a cane efficiently, (see FIGS. 1A and 1B). The handle and/or the smart mobility assistance device can have a wide range of sensors that detects biometrics including but not limited to:

Blood work
Blood Pressure:
Blood sugar
Heart Rate
Oxygen level/rate
ECG: electrical activity in your heart: it could be done by a single handle using only one hand, or by two handles using to hands on some devices like walkers.
EMG
Muscle Strain
Humidity
UV
Body temperature Gripping sensor: it turn the cane on when user grip it and it turns it off when not used to save battery.

Light sensor: it can be used to detect if the cane lights should be turned on or not.

Fingerprint sensor: to identify the user of the device and sign-in, or sign out, him/her into his/her account to track their activities. That's mean; more than one user can use the device without affecting each other's online records.

GPS: with a turn-by-turn visual, voice and vibration guidance. Also, it can be used to locate the device using a cell phone or a tablet and command it to create a sound or to lock it. In addition, it can be used outdoor or indoor.

Status indicator: in the form of a light, LED light, sound, vibration or/and screen, that can be on the handle or any place on the mobility device that indicates the health status of the user. For example, the light/screen can be green if the user metrics in the normal and healthy range, it can be yellow if there is some metrics that is not or it could be red Smart mobility aid device embodiments may also include a variety of activity tracking to make users healthier. A mobility aid device could have components including but not limited to those shown in FIG. 2 and may also include one or more of:

Accelerometer
Gyroscope
MEMS magnetometer
Barometric pressure sensor
Temperature sensor
Microcontroller
Flash memory
Digital Motion Processor for sensor fusion management
Motion Processing Library
Bluetooth low energy radio The device will count the number of steps, number of miles, type of activity, calories burned and based on the user weight t and it will provide the amount of calories burned. User weight can be determined by the user pressure on the cane, or by entering it on the cane screen or using smart devices such as a phone, a smart watch, a smart glass, a tablet.

The cane can give the users live feedback on their performance and motivate them to achieve targets.

In addition, it can create games for them based on their own targets, or/and it will have the social gaming by comparing them and make them compete with other people.

The cane can train users to walk in the right way and advise them if they walk in an unhealthy way.

Some Motions and Gestures:

Step count: measures step counts from time t1 to time t2.

Tap: detects a series n taps, n=1, 10, when taps occur within one second of each other.

Activity detector: using the t to determine the current activity detected by the motion sensors and provides the time t when this activity started. Activities are defined as walking, running, sitting, watching TV, going to bathroom and so on.

Shake (n, direction): gives the number of shakes detected within one second of each other in one direction and indicates the direction (x.y.z).

Rotation (degrees, direction): gives the number of degrees of rotation along one axis (x,y,z).

Glyph detect: detects a glyph already stored as a "trained" glyph.

Swipe (direction): detects a swipe motion in one of the x, y, or z directions.

There is also provided an interface connector for controlling external sensors, I/O and debug.

The system functions include but are not limited to:
Linear acceleration
Heading
Altitude
Temperature
Angular velocity
Angular position A smart mobility aid device may also include features to make users more independent:

Utilizing the above sensor capabilities, the smart mobility aid device will create a daily activity pattern of the user. If there is any unexpected change on the patterns, the device will send the caregiver a notification.

The device will be collecting the information about user's activities and will create a pattern. The device will notify caregiver if there's any changes on the daily patterns of the user.

An emergency button for user to press to communicate with one or more caregiver, or to dial 911. The communication could in the different forms including but not limited to a phone call, app push notification, third parties, or/and website update.

Emergency notification to caregiver/s or/and alarm in case the user falls down. Artificial intelligence algorithm with motion sensors differentiates if the user falls or the device is just dropped.

The device can alert user for natural disasters such as earthquake and high wind.

Pressure & motion sensors: monitoring user pressure on the device. The device can help user monitor their leg strength based on the pressure placed on the device, combining different metrics will allow the device to give advice for users regarding their rehabilitation situation, their way of walking and how to improve it, or it can suggest using different smart mobility aid device like a walker instead of a cane. The motion sensors can track user activities even if they are not using them, such as sleeping, and creates activity patterns.

Additional features of smart mobility aid devices:

Distance sensor (ultrasonic) to warn users against objects or obstacles. For instance, warning before stairs or steps.

Black Box that saves the past activities such as sound, vibrations and activities. It will be anti-fire and explosion.

The device can be integrated with mobile payment systems, which allows the user to use it as a payment method rather than cash or credit.

Medication Management:

The device alarms, notifies and reminds users about their medication schedule by voice reminders, vibration and/or using a screen. When the user takes the medication, the caregiver or any involved parties will get notified. User, caregiver or doctors can enter, manage, update and/or track the medication schedule.

The device can communicate and connect to a regular or smart medication containers.

All the above sensors and components could be distributed into the body of a smart mobility cane, or different kinds of smart mobility devices such as walkers, wheelchairs, scooters or crutches, if needed.

Body Feature:

The cane will have a low power lighting part or a glowing color that light in the dark to enable users to find the cane in dark places and hold it easy.

The cane will have a light that will be turned on automatically in the case its on a dark place (using the light sensor) and the user is grabbing the handle.

The cane can be folded to reduce its size. The cane includes a spring to make it automatically unfold when pressing the unfolding button. It can include a damper to make the unfolding motion smoother.

Figure 3:
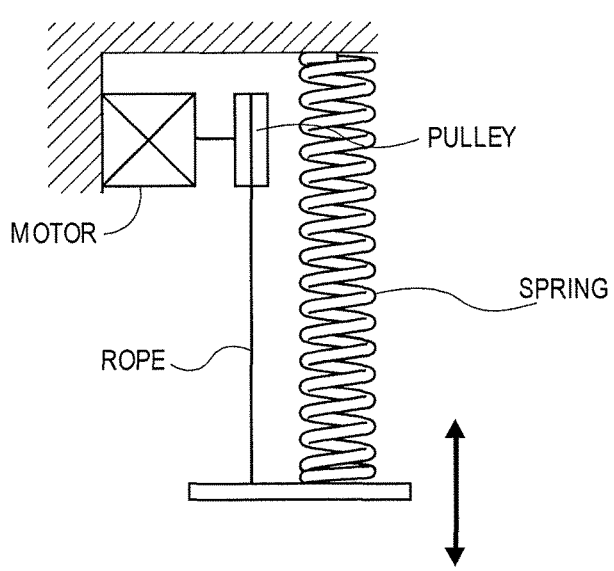
FIG. 3 is a side view of an embodiment of an automatic lifting mechanism.

The cane can be folded/unfolded automatically using a small light motor with folding/unfolding mechanism. The folding/unfolding mechanism could include a small motor, rope mechanism with a spring. This could be done manually or automatically once the user holds the cane. (see FIG. 3).

The cane can generate a sound to allow user to identify its place. In addition, it can be located by a GPS system using the cell phone.

Changeable cane base/tip: the bottom end of the cane body is designed in a way that allows an easy replacement process of the cane base. It includes a self-locking/clipping mechanism. The base tip can be replaced based on the preference, the condition of the user and the environment that it will be used on. It have several designs including but not limited to basic base, tripod base to make it stand alone, flexible, ice tip and so on.

Data Representation:

Collected information and data could be presented and communicated to the user by a built-in screen/touch-screen or/and by voice or/and vibration or/and using a different electronic devices including but not limited to smart phones, smart watches or smart glasses.

Embodiments of the smart mobility aid devices described herein also allow other parties such as caregiver or doctors can have a live access to the mobility aid device information to monitor all the metrics. In this way, other parties may take actions, give advice, help or interact with the user.

In some embodiments, a mobility aid device could have a microphone and a speaker to allow a two-way communication with caregiver, a doctor, or an access to medical store services such as someone tells stories and talks to the user.

The data can be communicated in different forms including but not limited to a visual form, a sound form, or/and a vibration form.

Data Communication:

The collected data will be synced seamlessly, transferred, updated and communicated using a low power communication such as Bluetooth or/and Wi-Fi technologies. The device could include a SIM card to keep it connected outdoor. In addition, the device could directly connect to the user's smartphone without the need of a SIM card on the device itself. See FIGS. 4, 5, and 6 that illustrate various alternative communication methods.

In still other embodiments, a smart mobility aid device could be connected to different electronic devices. In one aspect, a smart mobility aid device user can have metrics or more than one device. For example, a smart cane can communicate with more than one device such as smart walkers, smart crutches or smart wheelchairs.

Data Analysis:

The data obtained from the sensor can be analyzed on the device itself, on the phone, or/and on the cloud. The analysis will include predictive analysis that leads to recommendations for users, caregiver or any interested party. Also, there will be pattern visualization and data integrate with third parties. Based on the data representation and analysis, the user, caregiver or/and the doctor can monitor, take actions or/and communicate with the user.

Figure 8:
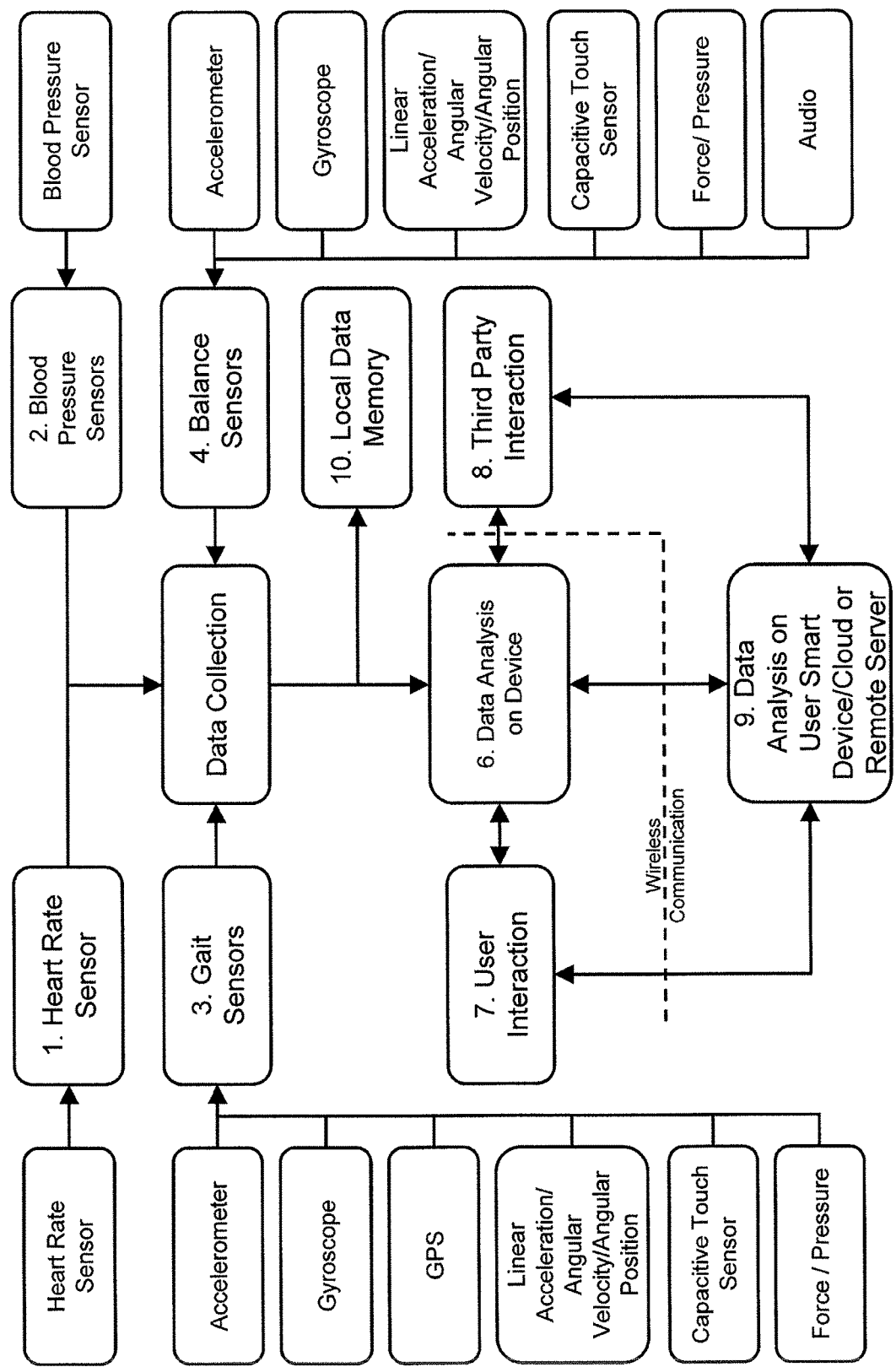
FIG. 8 is a schematic representation of sensor data collection and analysis on a smart mobility aid device.

An exemplary overall process of smart mobility device user activity data collection, analysis and communication is illustrated in FIG. 8. Data signals collected (5), for example, for use by the system for predictive analysis and recommendations for a user's rehabilitation or way of walking include heart rate (1), blood pressure (2), gait (3), and balance (4). Data analysis may be performed on the device (6) or on a user smart device or the cloud or remote server. Thereafter, the analysis and representation of the data may then lead to user interaction (7) and/or third party interaction (8) including but not limited to activity tracking, biometrics and safety and emergency features. The activity tracking may include the number of steps, miles or activity speed, user pressure on a smart mobility device or activity types. The sensor data and analysis may also be used for fall detection and warnings, user pattern analysis and user pattern changes. The system may analyze how a user walks and advise the user on how to improve the walking pattern. The data on how to improve may be represented in the form of visuals, sound/voice, or vibrations. The smart mobility device may also give the user or/and caregiver a live feedback about the user health metrics and status using a data representation method.

Once the assessment is made, the central processing unit may interact with the device user or third parties, primarily in the case of a recent actual or predicted fall. This interaction may be made directly through the device, such as a notification light, sound, vibration, or display for the user (7). It can also directly contact third parties (8) utilizing wireless connections (e.g. Wi-Fi, Bluetooth, SIM, cellular) for notification (e.g. a call, push notification, text, alert, smartphone, etc.) on other devices. The central processing unit may also utilize the cloud, smart device or caregiver smart device (See FIGS. 4, 5, and 6) as a conduit for communication and alerts with the device user and third parties to reach them on other devices or systems (e.g. web portal, call, smartphone, text, etc.).

Figure 2:
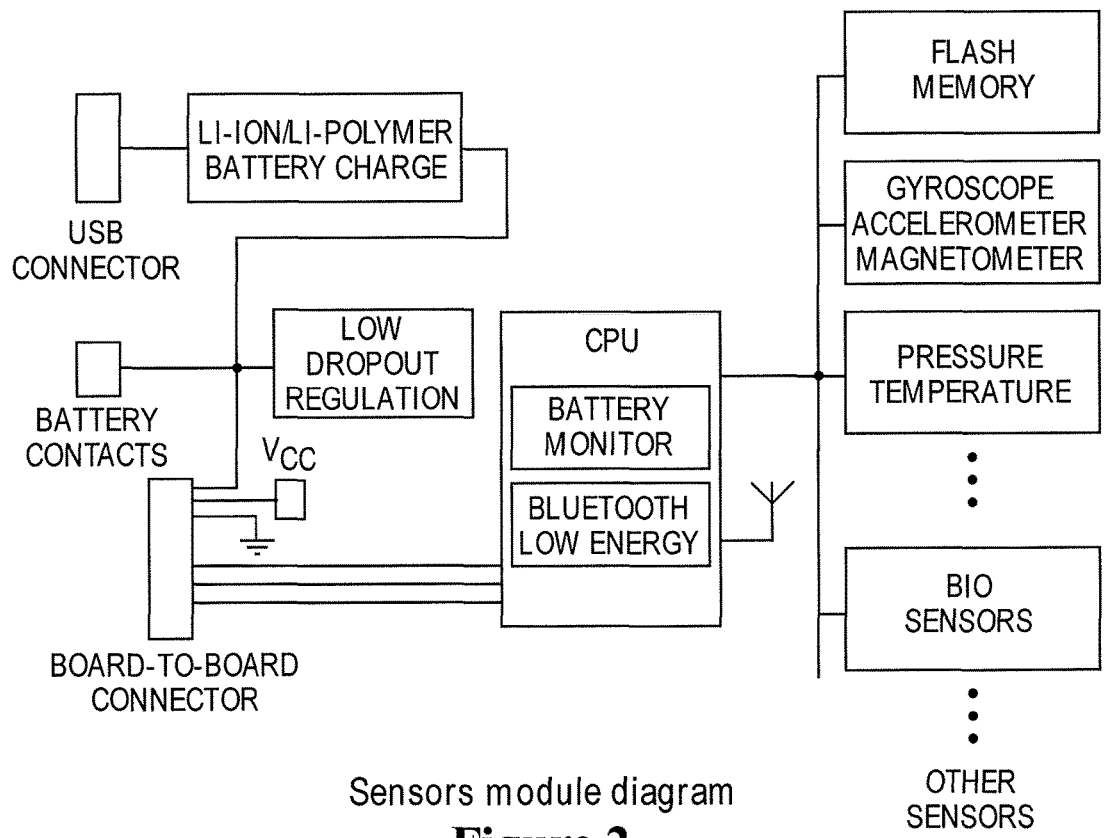
FIG. 2 is a schematic diagram of an exemplary electronics and sensor module.

Power Source:

The device could have a lightweight rechargeable lithium battery or a one-time long-life battery that does not requires charging (see FIG. 2). In case of the rechargeable battery, the user will only need to place the cane in an upward position— using position—on the charger (charging pad) to get charged. The cane can be charged wirelessly or by self plugged magnetic plug. In addition to that, it can have a self-charging mechanism generated by movements. Also, it can have a Li-ion-polymer battery charger and management via Micro-USB or a regular USB.

Figure 7A:
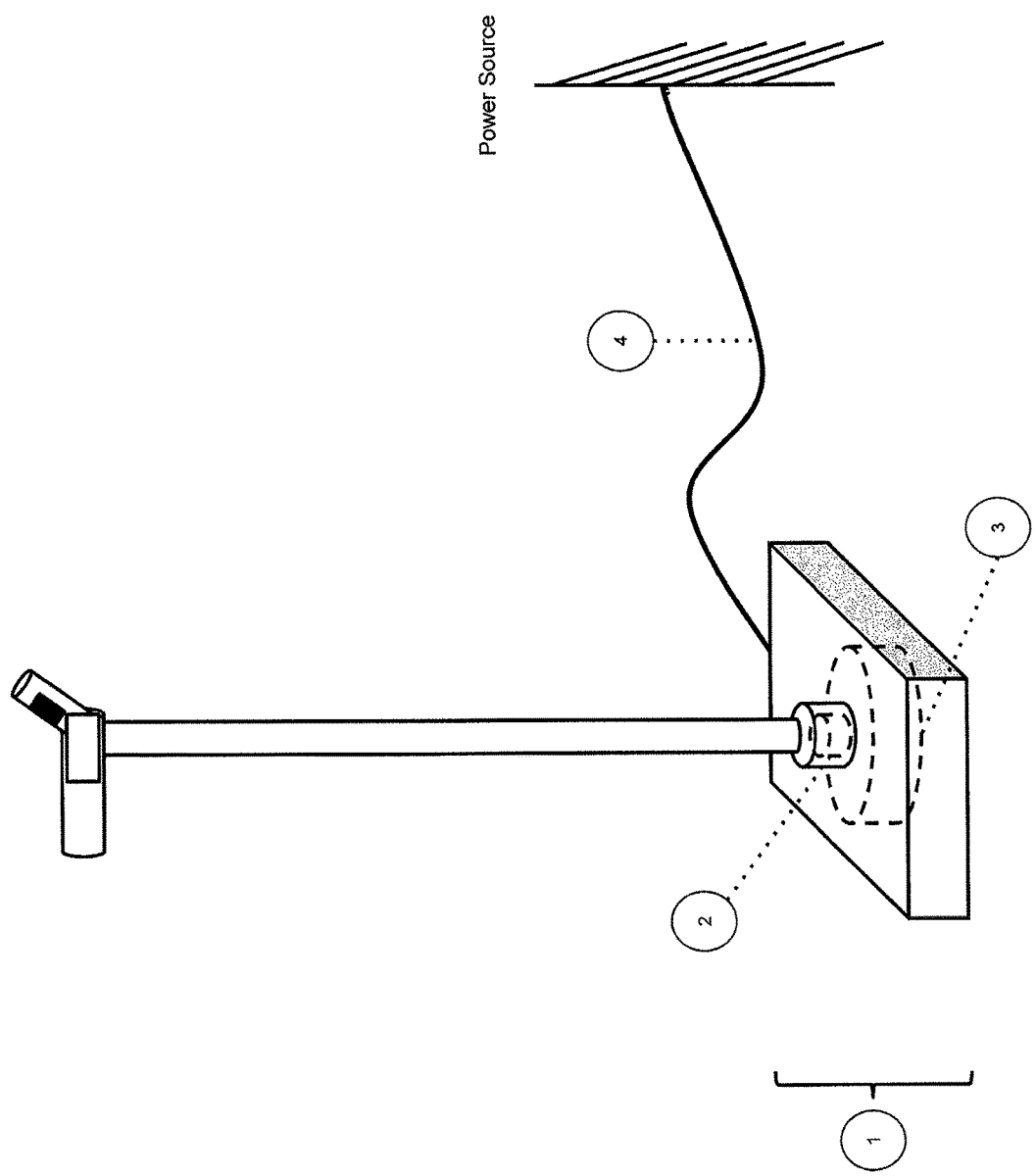
FIG. 7A is a perspective view of a smart cane embodiment on a wireless charger base.

The smart mobility aid devices may be charged wirelessly via induction or wireless charging. FIG. 7A illustrates a smart cane on a wireless charging pad (1). The base 3 of the cane contains an induction charging coil (2) to receive power from the coil inside the charging pad (3). The charging pad is connected by electrical wires (4) to a power source, such as a wall outlet or USB port. The cane can be set on the pad to charge and removed from the pad without connecting or attaching any wires.

Figure 7C:
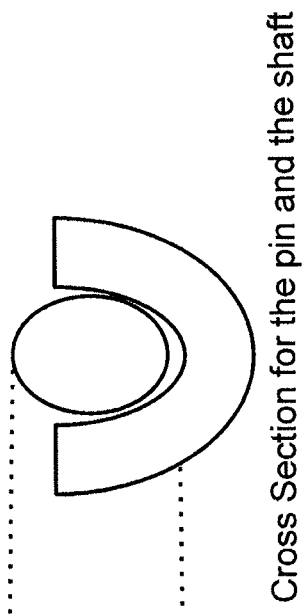
FIGS. 7B and 7C are perspective and top down views of a charger and a self-plugged magnetic plug.
Figure 7B:
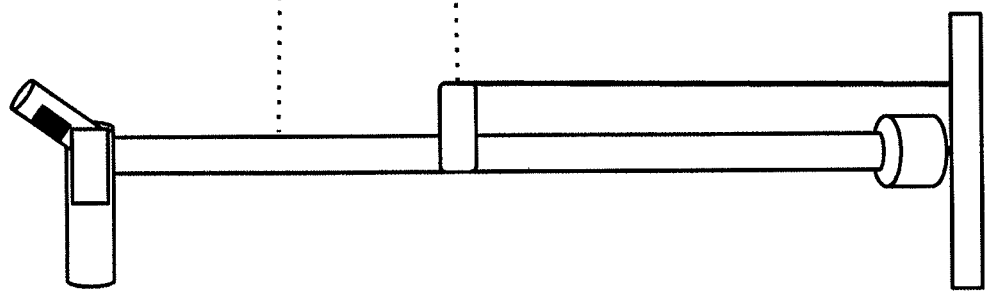

The charger can snap into the smart device body for easier attachment as shown in FIGS. 7B and 7C. The connection to the smart device body may include a self plugged magnetic plug.

Store for Services:

The mobility aid devices will have access to a mobility aid device software platform, an app store, where people can develop apps and services to offer for our users. In addition, there is an open API for developers to include additional features to use with a mobility aid device.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions.

For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A multifunctional smart cane, comprising:
    a handle adapted to be gripped by a hand of a user;
    a body having a base on one end and coupled to the handle on the other;
    a light operable by a light sensor;
    a display built into the handle wherein the display is visible to the user while gripping the handle;
    one or more activity tracking components carried by the smart cane for collecting information about the user's daily activity;
    an electronic memory for storing the collected information about the user's daily activity; and
    one or more electronic communication components to transmit the user's daily activity from the electronic memory in the smart cane to another electronic device.

2. The smart cane of claim 1 wherein the handle includes a gripping sensor used to power on and power off the smart cane when the smart cane user grips the gripping sensor.

3. The smart cane of claim 1 wherein the one or more electronic components is a SIM card, a Wi-Fi communications module or a Bluetooth communications module.

4. The smart cane of claim 1 wherein the one or electronic communication components provides communication using a cellular network, an app push notification, a third party update or a website update.

5. The smart cane of claim 1 wherein the one or electronic communication components provides for entering user data into the smart cane using a smartphone, a smart watch, a smart glass or a tablet.

6. The smart cane of claim 1 wherein a rechargeable battery within the smart cane is adapted and configured for wireless charging, or for charging via a self-plugging magnetic plug.

7. The smart cane of claim 1 further comprising a sensor for detecting a biometric measurement of the smart cane user selected from blood work, blood pressure, blood sugar, heart rate, oxygen level/rate, ECG, EMG, muscle strain, humidity, UV or body temperature.

8. The smart cane of claim 1 further comprising one or more smart cane user activity tracking components selected from an accelerometer, a gyroscope, a MEMS magnetometer, a barometric pressure sensor, a temperature sensor, a microcontroller, a flash memory, a digital motion processor, a motion processing library, a Bluetooth low energy radio component, a motion sensor, a pressure sensor on the cane, or a sensor configured to detect a weight imparted by the user upon the smart cane.

9. The smart cane of claim 1 the collected information about the user's daily activity further comprising: a linear acceleration, a heading, an altitude, a temperature, an angular velocity, or an angular position.

10. The smart cane of claim 1 wherein the light comes on automatically when the light sensor detects darkness.

11. The smart cane of claim 1 the cane further comprising a base changing mechanism allowing for removal of the base and replacement with a different base.

12. The smart cane of claim 1 wherein a user preference or smart cane advice determines the removal of the base and the replacement with a different base.

13. The smart cane of claim 12 wherein the base and the different base are selected from a basic base, a tripod base, a flexible base and an ice tip base.

14. The smart cane of claim 1 further comprising a sensor configured to detect an audio signal from the user or an emergency button that when pressed establishes communications with one or more of a caregiver or a 911 emergency service.

15. The smart cane claim 1 the display providing a health status indicator of the user in the form of a light, an LED light, a sound, a vibration, or a glyph.

* * * * *